United States Patent
Liao et al.

(10) Patent No.: US 11,858,891 B2
(45) Date of Patent: Jan. 2, 2024

(54) DECOLORIZATION AND PURIFICATION METHOD OF BHET MATERIAL

(71) Applicant: NAN YA PLASTICS CORPORATION, Taipei (TW)

(72) Inventors: Te-Chao Liao, Taipei (TW); Jung-Jen Chuang, Taipei (TW); Yu Ti Tseng, Taipei (TW); Zhang-Jian Huang, Taipei (TW)

(73) Assignee: NAN YA PLASTICS CORPORATION, Taipei (TW)

( * ) Notice: Subject to any disclaimer, the term of this patent is extended or adjusted under 35 U.S.C. 154(b) by 0 days.

(21) Appl. No.: 17/570,351

(22) Filed: Jan. 6, 2022

(65) Prior Publication Data

US 2023/0147792 A1  May 11, 2023

(30) Foreign Application Priority Data

Nov. 8, 2021  (TW) .................. 110141568

(51) Int. Cl.
| | |
|---|---|
| *C07C 67/52* | (2006.01) |
| *B01J 20/20* | (2006.01) |
| *B01D 15/08* | (2006.01) |
| *B01D 9/00* | (2006.01) |
| *C07C 67/48* | (2006.01) |
| *C07C 67/60* | (2006.01) |

(52) U.S. Cl.
CPC ............ *C07C 67/52* (2013.01); *B01D 9/0004* (2013.01); *B01D 15/08* (2013.01); *B01J 20/20* (2013.01); *C07C 67/48* (2013.01); *C07C 67/60* (2013.01); *B01D 2009/0086* (2013.01)

(58) Field of Classification Search
CPC ......... C07C 67/48; C07C 67/52; C07C 67/60; C07C 69/82; B01D 9/0004; B01D 2009/0086; B01J 20/20
See application file for complete search history.

(56) References Cited

FOREIGN PATENT DOCUMENTS

| CN | 105367425 a | * | 3/2016 | ............. C07C 67/48 |
|---|---|---|---|---|
| CN | 107266664 | | 10/2017 | |
| JP | 2016536291 | | 11/2016 | |
| WO | 2021124149 | | 6/2021 | |
| WO | WO-2021124149 A1 | * | 6/2021 | ............. C07C 67/56 |

OTHER PUBLICATIONS

CN105367425 (A), Li Feng et al., Purification system for chemical method for preparing BHET monomer from waste PET material, English translation, 8 pages (Year: 2016).*
Huang J. et al., Removal of trace amount impurities in glycolytic monomer of polyethylene terephthalate by recrystallization, Journal of Environmental Chemical Engineering, vol. 9, No. 5, 106277, pp. 1-8 (on line Aug. 25, 2021) (Year: 2021).*
"Office Action of Japan Counterpart Application", dated Oct. 3, 2023, p. 1-p. 2.

* cited by examiner

Primary Examiner — Yate' K Cutliff
(74) Attorney, Agent, or Firm — JCIPRNET

(57) ABSTRACT

The disclosure provides a decolorization and purification method of BHET material, which includes the following steps. A first dose of activated carbon is added to preliminarily treat the BHET material. After the preliminary treatment, a first cooling crystallization process and filtration are performed to obtain BHET crystals. Afterwards, an oxidant is used to chemically react with the BHET crystals to destroy a dye or impurities, and then a second dose of activated carbon is added to adsorb a chemically reacted oxide. Next, a second cooling crystallization process, filtration, and drying are performed to obtain a finished product of BHET.

10 Claims, No Drawings

DECOLORIZATION AND PURIFICATION METHOD OF BHET MATERIAL

CROSS-REFERENCE TO RELATED APPLICATION

This application claims the priority benefit of Taiwan application serial no. 110141568, filed on Nov, 8, 2021. The entirety of the above-mentioned patent application is hereby incorporated by reference herein and made a part of this specification.

BACKGROUND

Technical Field

The disclosure relates to a decolorization and purification method, and more particularly, to a decolorization and purification method of BHET material.

Description of Related Art

Regarding the chemical recycling method of waste PET (polyethylene terephthalate) fabrics, ethylene glycol (EG) is usually used to depolymerize PET into crude BHET (bis(2-Hydroxyethyl) terephthalate), and then the crude BHET is decolorized and purified to obtain a clean white finished product of BHET. However, the waste PET fabrics often contain impurities such as textile auxiliaries and dyes. Especially after depolymerization of PET, the dyes are usually compatible with BHET and difficult to separate, resulting in relatively poor hue of the finished product of BHET.

Based on the above, it is an important issue for current research to develop a decolorization and purification method of BHET material, so as to improve the hue of the finished product of BHET.

SUMMARY

The disclosure provides a decolorization and purification method of BHET material, which may decolorize and purify BHET formed by depolymerization of various waste PET fabrics to obtain a clean white finished product of BHET.

The decolorization and purification method of the BHET material in the disclosure includes the following steps. A first dose of activated carbon is added to preliminarily treat the BHET material. After the preliminary treatment, a first cooling crystallization process and filtration are performed to obtain BHET crystals. Afterwards, an oxidant is used to chemically react with the BHET crystals to destroy a dye or impurities, and then a second dose of activated carbon is added to adsorb a chemically reacted oxide. Next, a second cooling crystallization process, filtration, and drying are performed to obtain a finished product of BHET.

In an embodiment of the disclosure, a CIELAB color of the finished product of BHET is defined as having an L value of 95 or more, an a value of −1.0 to 1.0, and a b value of 4.0 or less.

In an embodiment of the disclosure, based on a total weight of the BHET material, the first dose is 0.5 wt % to 8 wt %.

In an embodiment of the disclosure, a treatment temperature of the preliminary treatment is 80° C. to 90° C.

In an embodiment of the disclosure, the oxidant includes hydrogen peroxide, calcium hypochlorite, or sodium hydrosulfite.

In an embodiment of the disclosure, based on the total weight of the BHET material, an additive amount of the oxidant is 0.1 wt % to 1 wt %.

In an embodiment of the disclosure, a reaction temperature of the chemical reaction is 80° C. to 90° C.

In an embodiment of the disclosure, based on the total weight of the BHET material, the second dose is 0.1 wt % to 3 wt %.

In an embodiment of the disclosure, a treatment temperature of adding the second dose of activated carbon is 80° C. to 90° C.

In an embodiment of the disclosure, a process temperature of the first cooling crystallization process and the second cooling crystallization process is 20° C.

Based on the above, the decolorization and purification method of the BHET material in the disclosure is optimized in the specific sequence of steps. A total of four procedural steps are included in sequence, which may decolorize and purify BHET formed by the depolymerization of various waste PET fabrics to obtain clean white BHET. Especially for the dark BHET material with the impurities such as textile auxiliaries and the dye, the dye and the impurities that are difficult to remove may be completely destroyed and removed, so as to effectively improve the hue of the finished product of BHET.

DETAILED DESCRIPTION OF DISCLOSED EMBODIMENTS

Hereinafter, embodiments of the disclosure will be described in detail. However, these embodiments are illustrative, and the disclosure is not limited thereto.

In the present specification, a range represented by "a numerical value to another numerical value" is a schematic representation for avoiding listing all of the numerical values in the range in the specification. Therefore, the recitation of a specific numerical range covers any numerical value in the numerical range and a smaller numerical range defined by any numerical value in the numerical range, as is the case with any numerical value and a smaller numerical range thereof in the specification.

The disclosure provides a decolorization and purification method of BHET material, which sequentially includes the following four procedural steps. The first procedural step is that a first dose of activated carbon is added to preliminarily treat the BHET material. The second procedural step is that after the preliminary treatment, a first cooling crystallization process and filtration are performed to obtain BHET crystals. The third procedural step is that an oxidant is used to chemically react with the BHET crystals to destroy a dye or impurities, and then a second dose of activated carbon is added to adsorb a chemically reacted oxide. The fourth procedural step is that a second cooling crystallization process, filtration, and drying are performed to obtain a finished product of BHET.

In the first procedural step, solvent extraction is used to identify an impurity content in the BHET material, and based on this, an additive amount of the activated carbon for the preliminary treatment (the first dose of activated carbon) is determined. In this embodiment, the BHET material is, for example, dark BHET material, and a CIELAB color is, for example, defined as having an L value of 30 to 45, an a value of −1 to −3, and a b value of −2 to −4. The solvent extraction is, for example, to extract a PET fabric with an alcohol ether solvent. A weight ratio of the alcohol ether solvent to the PET fabric is, for example, 20:1, and a reaction condition is, for example, at a temperature of 140° C. for 2 hours. Based on a total weight of the PET fabric, the minimum extracted impurity content is, for example, 0.2 wt % to 1 wt %. In this embodiment, based on a total weight of the BHET material, the first dose of activated carbon is, for example, 0.5 wt % to 8 wt %, and a treatment temperature and time of the preliminary treatment are, for example, at 80° C. to 90° C. for 3 hours. For example, the preliminary treatment of the activated carbon is performed after adding water. Afterwards, the filtration is performed to remove the activated carbon.

In the second procedural step, a process temperature of the first cooling crystallization process is, for example, 20° C., and the first cooling crystallization process and the filtration are performed for 6 hours to obtain the BHET crystals while trace impurities are removed to an aqueous phase.

In the third procedural step, the oxidant may include hydrogen peroxide, calcium hypochlorite, or sodium hydrosulfite. Based on the total weight of the BHET material, an additive amount of the oxidant is, for example, 0.1 wt % to 1 wt %, and a reaction temperature and time for the chemical reaction of the BHET crystals using the oxidant is, for example, at 80° C. to 90° C. for 1 hour. For example, the oxidant is used to chemically react after adding the water to destroy the dye or the impurities that are difficult to remove. In this embodiment, based on the total weight of the BHET material, the second dose of activated carbon is, for example, 0.1 wt % to 3 wt %, and a treatment temperature and time of adding the second dose of activated carbon are, for example, at 80° C. to 90° C. for 3 hours to adsorb the chemically reacted oxide, and then completely remove the impurities. Afterwards, the filtration is performed to remove the activated carbon.

In the fourth procedural step, a process temperature of the second cooling crystallization process is, for example, 20° C., and the second cooling crystallization process, filtration, and drying are performed for 6 hours, while the trace impurities are removed to the aqueous phase, so as to obtain the BHET crystals. For the obtained finished product of BHET, the CIELAB color is, for example, defined as having the L value of 95 or more, the a value of −1.0 to 1.0, and the b value of 4.0 or less. Therefore, according to the decolorization and purification method of the BHET material in the disclosure, the dark BHET material may be decolorized and purified to obtain clean white BHET.

Based on the above, the decolorization and purification method of the BHET material in the disclosure is optimized in the specific sequence of steps. A total of four procedural steps are included in sequence, which may decolorize and purify BHET formed by the depolymerization of various waste PET fabrics to obtain clean white BHET. Especially for the dark BHET material with the impurities such as textile auxiliaries and the dye, the dye and the impurities that are difficult to remove may be completely destroyed and removed, so as to effectively improve the hue of the finished product of BHET. The CIELAB color of the finished product of BHET is defined as having the L value of 95 or more, the a value of −−1.0 to 1.0, and the b value of 4.0 or less.

What is claimed is:

1. A decolorization and purification method of BHET (bis(2-Hydroxyethyl) terephthalate) material, comprising:
    adding a first dose of activated carbon to preliminarily treat the BHET material;
    after the preliminary treatment, performing a first cooling crystallization process and filtration to obtain BHET crystals;
    using an oxidant to chemically react with the BHET crystals to destroy a dye or impurities, and then adding a second dose of activated carbon to adsorb a chemically reacted oxide; and
    performing a second cooling crystallization process, filtration, and drying to obtain a finished product of BHET.

2. The decolorization and purification method of the BHET material according to claim 1, wherein a CIELAB color of the finished product of BHET is defined as having an L value of 95 or more, an a value of −1.0 to 1.0, and a b value of 4.0 or less.

3. The decolorization and purification method of the BHET material according to claim 1, wherein based on a total weight of the BHET material, the first dose is 0.5 wt % to 8 wt %.

4. The decolorization and purification method of the BHET material according to claim 1, wherein a treatment temperature of the preliminary treatment is 80° C. to 90° C.

5. The decolorization and purification method of the BHET material according to claim 1, wherein the oxidant comprises hydrogen peroxide, calcium hypochlorite, or sodium hydrosulfite.

6. The decolorization and purification method of the BHET material according to claim 1, wherein based on a total weight of the BHET material, an additive amount of the oxidant is 0.1 wt % to 1 wt %.

7. The decolorization and purification method of the BHET material according to claim 1, wherein a reaction temperature of the chemical reaction is 80° C. to 90° C.

8. The decolorization and purification method of the BHET material according to claim 1, wherein based a total weight of the BHET material, the second dose is 0.1 wt % to 3 wt %.

9. The decolorization and purification method of the BHET material according to claim 1, wherein a treatment temperature of adding the second dose of activated carbon is 80° C. to 90° C.

10. The decolorization and purification method of the BHET material according to claim 1, wherein a process temperature of the first cooling crystallization process and the second cooling crystallization process is 20° C.

* * * * *